United States Patent
Philipp et al.

(10) Patent No.: US 10,426,562 B1
(45) Date of Patent: Oct. 1, 2019

(54) WEARABLE MULTI-ACCESSORY TOOL FOR NURSES AND OTHER HEALTH CARE WORKERS

(71) Applicants: Linda Philipp, Boca Raton, FL (US); Bernard Philipp, Boca Raton, FL (US)

(72) Inventors: Linda Philipp, Boca Raton, FL (US); Bernard Philipp, Boca Raton, FL (US)

( * ) Notice: Subject to any disclaimer, the term of this patent is extended or adjusted under 35 U.S.C. 154(b) by 0 days.

(21) Appl. No.: 15/385,123

(22) Filed: Dec. 20, 2016

Related U.S. Application Data (60) Provisional application No. 62/272,537, filed on Dec. 29, 2015.

(51) Int. Cl.
| | | |
|---|---|---|
| A61B 17/3201 | (2006.01) |
| A61B 50/31 | (2016.01) |
| A45F 5/02 | (2006.01) |
| B65D 83/08 | (2006.01) |
| B65D 85/67 | (2006.01) |
| A61J 7/00 | (2006.01) |
| A61B 90/30 | (2016.01) |
| F21V 23/04 | (2006.01) |
| F21V 33/00 | (2006.01) |
| A61B 50/30 | (2016.01) |

(Continued)

(52) U.S. Cl.
CPC .............. *A61B 50/31* (2016.02); *A45F 5/021* (2013.01); *A61B 17/3201* (2013.01); *A61B 90/30* (2016.02); *A61J 7/0007* (2013.01); *B65D 83/0811* (2013.01); *B65D 85/67* (2013.01); *F21V 23/0414* (2013.01); *F21V 33/0068* (2013.01); *A61B 2050/301* (2016.02); *A61B 2050/3008* (2016.02); *A61B 2050/311* (2016.02); *A61B 2090/309* (2016.02); *F21W 2131/20* (2013.01); *F21Y 2115/10* (2016.08)

(58) Field of Classification Search
CPC ..... A61B 17/3201; A61B 90/30; A61B 50/31; A61B 2050/3008; A61B 2050/301; A61B 2050/311; B65D 83/0811; B65D 85/67; A45F 5/021; F21V 33/0068
See application file for complete search history.

(56) References Cited

U.S. PATENT DOCUMENTS

| | | | | |
|---|---|---|---|---|
| 5,358,158 A | * | 10/1994 | Darr ....................... | A01K 89/00 224/162 |
| 5,497,904 A | * | 3/1996 | Jones .................... | A01K 87/06 221/185 |

(Continued)

*Primary Examiner* — Derek J Battisti
(74) *Attorney, Agent, or Firm* — Glenn E. Gold, P.A.; Glenn E. Gold (57) ABSTRACT

A wearable healthcare multi-accessory tool includes a truncated conical body adapted to support health care attachment and illumination accessories, and an elongated tubular shaft having an interior open cavity and a lower opening to enable insertion of at least one of a hemostat and scissor into the shaft. The shaft supports the body about the shaft in a displaced relationship above the lower opening of the shaft so as to provide an annular space surrounding the shaft below and recessed relative to the body exterior so as to enable incorporation of a roll of health care tape into the annular space being rotatable about the shaft to enable a strip of the health care tape to be pulled and severed from the roll. The shaft also has at least one protrusion thereon adjacent to the lower opening to support the roll of health care tape about the shaft in the annular space.

20 Claims, 10 Drawing Sheets

(51) Int. Cl.
*F21Y 115/10* (2016.01)
*F21W 131/20* (2006.01)

(56) References Cited

U.S. PATENT DOCUMENTS

| | | | | |
|---|---|---|---|---|
| 5,641,109 | A * | 6/1997 | Willoughby | B65H 35/0026 224/162 |
| 5,961,066 | A * | 10/1999 | Hambleton | B65H 35/0026 224/162 |
| 6,213,365 | B1 * | 4/2001 | Stocke | A41D 13/0012 224/223 |
| 6,491,191 | B1 * | 12/2002 | Cleveland | A45F 5/00 224/251 |
| 8,056,715 | B2 * | 11/2011 | Conklin | B25H 3/00 206/338 |
| 2015/0216290 | A1 * | 8/2015 | Moreau | A45F 5/14 224/250 |
| 2015/0282600 | A1 * | 10/2015 | Richards | A45F 5/021 224/195 |
| 2016/0297583 | A1 * | 10/2016 | Staeben | F21V 33/004 |

* cited by examiner

FIG. 10

WEARABLE MULTI-ACCESSORY TOOL FOR NURSES AND OTHER HEALTH CARE WORKERS

CROSS REFERENCE(S) TO RELATED APPLICATION(S)

This U.S. non-provisional patent application claims the benefit of U.S. provisional patent application No. 62/272,537, filed Dec. 29, 2015, which is incorporated by reference herein in its entirety.

FIELD OF THE INVENTION

The present invention relates to health care accessories, and, more particularly, is concerned with a wearable health care multi-accessory tool.

BACKGROUND OF THE INVENTION

A variety of different tools for holding various accessories frequently used by nurses and other health care personnel are known in the prior art. One such tool, disclosed in U.S. Pat. App. Pub. No. 2007/0205235, is a utility belt having clips attached about the belt from which various items, such as scissors, keys, roll of tape, pen holder and the like, can hang. Also the utility belt may support one or more pouches for containing other selected items. Another such tool, disclosed in U.S. Pat. No. 4,796,790, is a health care supply case that can hang from a belt or shoulder harness worn by medical personnel. The case has several panels attached on a back panel that are vertically offset from and overlapped with one another so as to form narrow pockets in which to position various items so that upper portions of the items are visible once a covering flap extending over the pockets is raised.

A drawback of hanging various accessories about a utility belt is that this enables their exposure, and makes them susceptible, to catching on other equipment or personnel due to the close-quarters environment in which many health care personnel need to work. A drawback to the use of narrow pockets in a medical supply case to hold accessories is that the pockets are typically not tailored to accommodate the particular accessories they hold and thus frequently exert either insufficient grip or too much grip on the particular accessories.

Accordingly, there remains a need in the art for an innovation that will overcome the deficiencies and problems that remain unsolved.

SUMMARY OF THE INVENTION

The present invention is directed to an innovation that overcomes the deficiencies of the known art and the problems that remain unsolved by providing a wearable health care multi-accessory tool that is designed to both hold and incorporate health care accessories within the multi-accessory tool.

In one aspect of the present invention, a wearable health care multi-accessory tool includes:
a body of a truncated conical configuration adapted to support a plurality of health care attachment and illumination accessories; and
an elongated shaft of a tubular configuration having an interior open cavity and a lower opening to enable insertion of at least one of a hemostat and scissor into the interior open cavity via the lower opening, the elongated shaft supporting the body about the elongated shaft in a displaced relationship above the lower opening of the elongated shaft so as to provide an annular space surrounding the elongated shaft below and recessed relative to the exterior of the body so as to enable incorporation of a roll of health care tape into the annular space such that the roll is rotatable about the elongated shaft to further enable a strip of health care tape to be pulled and severed from the roll.

In another aspect of the present invention, a wearable health care multi-accessory tool includes:
a body of a truncated conical configuration adapted to support a plurality of health care attachment and illumination accessories; and
an elongated shaft of a tubular configuration having an interior open cavity and a lower opening to enable insertion of at least one of a hemostat and scissor into the interior open cavity via the lower opening;
wherein the elongated shaft includes
an upper shaft portion extending through the body and having an internally threaded bottom end section, and
a lower shaft portion having an externally threaded top end section threaded into the internally threaded bottom end section of the upper shaft portion such that the lower shaft portion extends downward and in axial alignment with the upper shaft portion, the lower shaft portion also having a bottom end section extending downward from the top end section to the lower opening of the elongated shaft and at least one protrusion on the lower shaft portion adjacent to the lower opening such that the upper shaft portion supports the body about the upper shaft portion in a displaced relationship above the lower opening of the elongated shaft and the at least one protrusion on the lower shaft portion so as to provide an annular space surrounding the lower shaft portion below and recessed relative to the exterior of the body on the upper shaft portion to enable incorporation of a roll of health care tape in the annular space and supported on the at least one protrusion on the lower shaft portion adjacent to the lower opening such that the roll is rotatable about the lower shaft portion to further enable a strip of health care tape to be pulled and severed from the roll;
further wherein the body includes
a platform at a bottom end of the body having an annular configuration defining an interior opening such that the upper shaft portion extends through the interior opening of the platform,
an end cap at a top end of the body being mounted above a top end of the upper shaft portion such that the end cap is adapted to support at least one of the plurality of health care attachment and illumination accessories, and
a sidewall adapted to support the plurality of health care attachment and illumination accessories and being disposed between the platform and the end cap and surrounding the upper shaft portion.

In another aspect of the present invention, the sidewall of the body includes a plurality of sidewall panels each adapted to support at least one of the plurality of health care attachment and illumination accessories. The plurality of sidewall panels include a rear sidewall panel adapted to support a pill splitter, an upper front sidewall panel being removable from the body so as to expose a battery-powered LED light supported on the body and aligned to seat in an aperture in the upper front sidewall panel when replaced on said body, and a lower front sidewall panel being removable from the body so as to expose a switch button supported on the body and aligned to seat in an aperture in the lower front sidewall panel when replaced on the body, the switch button being operable to turn on and off the LED light. The rear sidewall panel also has an attachment receptacle on the exterior of the rear sidewall panel and a clip having an attachment hook selectively insertable and removable into and from the attachment receptacle.

In another aspect of the present invention, a wearable healthcare multi-accessory tool includes:
  a body of a truncated conical configuration adapted to support a plurality of health care attachment and illumination accessories; and
  an elongated shaft of a tubular configuration having an interior open cavity and a lower opening to enable insertion of at least one of a hemostat and scissor into the interior open cavity via the lower opening;
  wherein the elongated shaft includes
    an upper shaft portion extending through the body, the upper shaft portion having an internally threaded bottom end and an upper end section holding a magnet to releasably retain the at least one of the hemostat and scissor in the elongated shaft, and
    a lower shaft portion having an externally threaded top end section threaded into the internally threaded bottom end section of the upper shaft portion such that the lower shaft portion extends downward and in axial alignment with the upper shaft portion, the lower shaft portion also having a bottom end section extending downward from the top end section to the lower opening of the elongated shaft and at least one protrusion on the lower shaft portion adjacent to the lower opening such that the upper shaft portion supports the body about the upper shaft portion in a displaced relationship above the lower opening of the elongated shaft and the at least one protrusion on the lower shaft portion so as to provide an annular space surrounding the lower shaft portion below and recessed relative to the exterior of the body on the upper shaft portion to enable incorporation of a roll of health care tape in the annular space and supported on the at least one protrusion on the lower shaft portion adjacent to the lower opening such that the roll is rotatable about the lower shaft portion to further enable a strip of health care tape to be pulled and severed from the roll;
  further wherein said body includes
    a platform at a bottom end of the body having an annular configuration defining an interior opening such that the upper shaft portion extends through the interior opening of the platform,
    an end cap at a top end of the body being mounted above a top end of the upper shaft portion such that the end cap is adapted to support at least one of the plurality of health care attachment and illumination accessories, and
    a sidewall adapted to support the plurality of health care attachment and illumination accessories and being disposed between the platform and the end cap and surrounding the upper shaft portion;
  still further wherein the sidewall has an attachment receptacle on the exterior thereof and also comprising a clip having an attachment hook selectively insertable and removable into and from the attachment receptacle.

In another aspect of the present invention, the platform also has an exterior ledge of an annular configuration, and the upper shaft portion adjacent to the internally threaded bottom end section thereof has an outwardly protruding flange displaced above the exterior ledge of the platform so as to define an annular chamber inside the sidewall in which to house a tape measure so as to be extendible and retractable from and into the annular chamber. Also, the platform of the body adjacent to and below the exterior ledge thereof has a recess of an annular configuration and the sidewall of the body at a lower end thereof has an inwardly protruding rim that fits into the annular recess of the platform.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION

Figure 1:
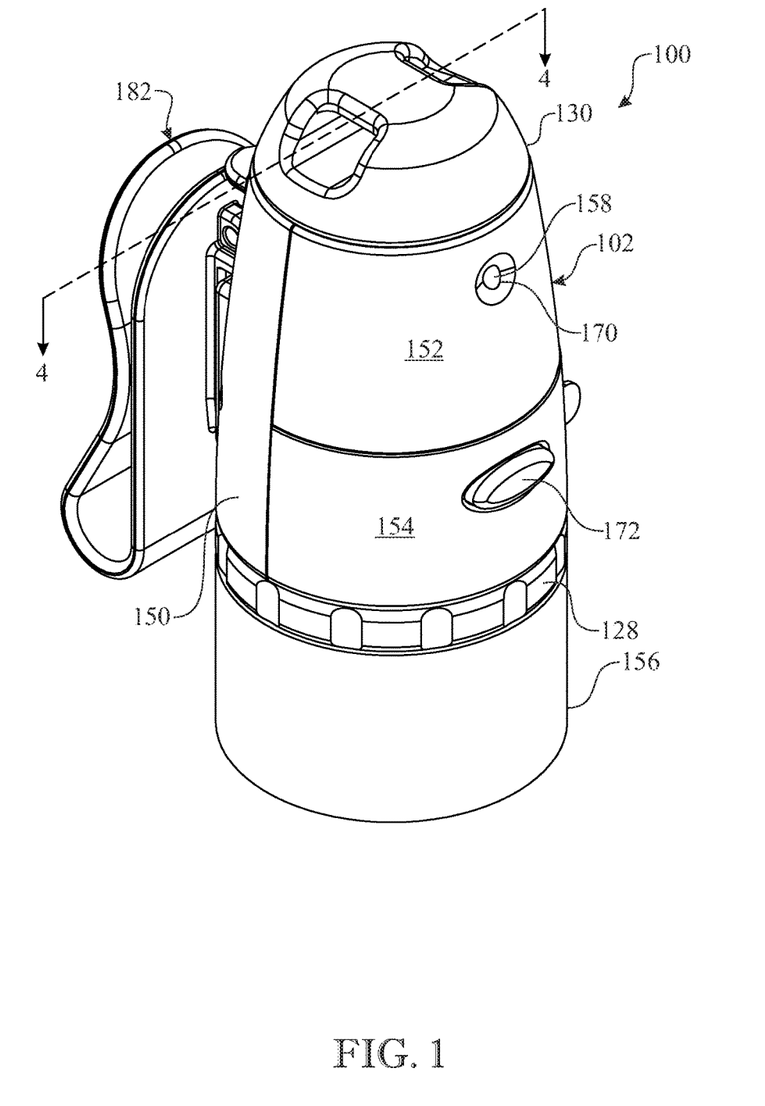
FIG. 1 presents a front isometric assembled view of an exemplary embodiment of a wearable health care multi-accessory tool in accordance with aspects of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Referring now primarily to FIGS. 1-6, there is illustrated an exemplary embodiment of a wearable multi-accessory tool particularly designed for use by certain personnel in the healthcare industry, generally designated as reference numeral 100, in accordance with aspects of the present invention. The wearable multi-accessory tool 100 has an elongated, generally truncated, conical configuration and incorporates a compact construction integrating some features and accessories into the tool body 102 itself, while releasably-securing (e.g., mounting) other healthcare-specific accessories and implements to the tool body, in a manner enabling immediate and efficient access thereto by an individual wearing the tool. For convenience, the terms "multi-accessory," "accessory," and "accessories" are used interchangeably throughout this application to generally reference any of the implements, features, accessories, and the like associated with the multi-accessory tool 100. As further elaborated herein, the various accessories are particularly useful to nurses and various other health care personnel for whom the ability to promptly access these accessories is particularly desirable. The multi-accessory tool 100 is uniquely constructed to be worn by a health care worker in a various forms, including being held within a scrub pocket, hung from a lanyard around the neck, and being clipped to a waistline, a pocket, or the like. Preferably, the multi-accessory tool 100 generally includes a body 102, or housing, having a truncated conical configuration, or geometry, particularly adapted to incorporate and/or support a plurality of the health care accessories, an elongated tubular shaft 104 extending through the interior of the body 102, along the body's central axis, and defining an elongated shaft interior, or cavity 106, having a lower opening 108 (i.e. an open lower end). The body 102 and elongated shaft 104 may be fabricated preferably from a lightweight material, such as a suitable plastic or metal.

More particularly, the elongated shaft 104 includes lower and upper shaft portions 110, 112 of tubular configurations defining interior lower and upper open cavities 114, 116. The lower and upper shaft portions 110, 112 interfit with one another such that their open cavities 114, 116 align in communication with one another and thereby form the interior open cavity 106 of the elongated shaft 104. The body 102 mounts about the upper shaft portion 112 of the elongated shaft 104, whereas the lower shaft portion 110 of the elongated shaft extends below the upper shaft portion. The upper shaft portion 112 extends through the body 102 and has an internally threaded bottom end section 118. The lower shaft portion 110 has an externally threaded top end section 120 threaded into the internally threaded bottom end section 118 of the upper shaft portion 112 such that the lower shaft portion extends downward from and in axial alignment with the upper shaft portion. The lower shaft portion 110 also has a bottom end section 122 that terminates at the lower opening 108 of the elongated shaft 104 and has a pair of opposite slots 124 formed in and extending upwardly on opposing sides of the bottom end section 122 of the lower shaft portion 110 from the lower opening 108 and terminating at the externally threaded top end section 120 of the lower shaft portion. The lower shaft portion 110 of the elongated shaft 104 also has at least one and preferably a pair of protrusions 126 thereon adjacent to the lower opening 108 that oppositely project radially outward from the lower opening.

Figure 2:
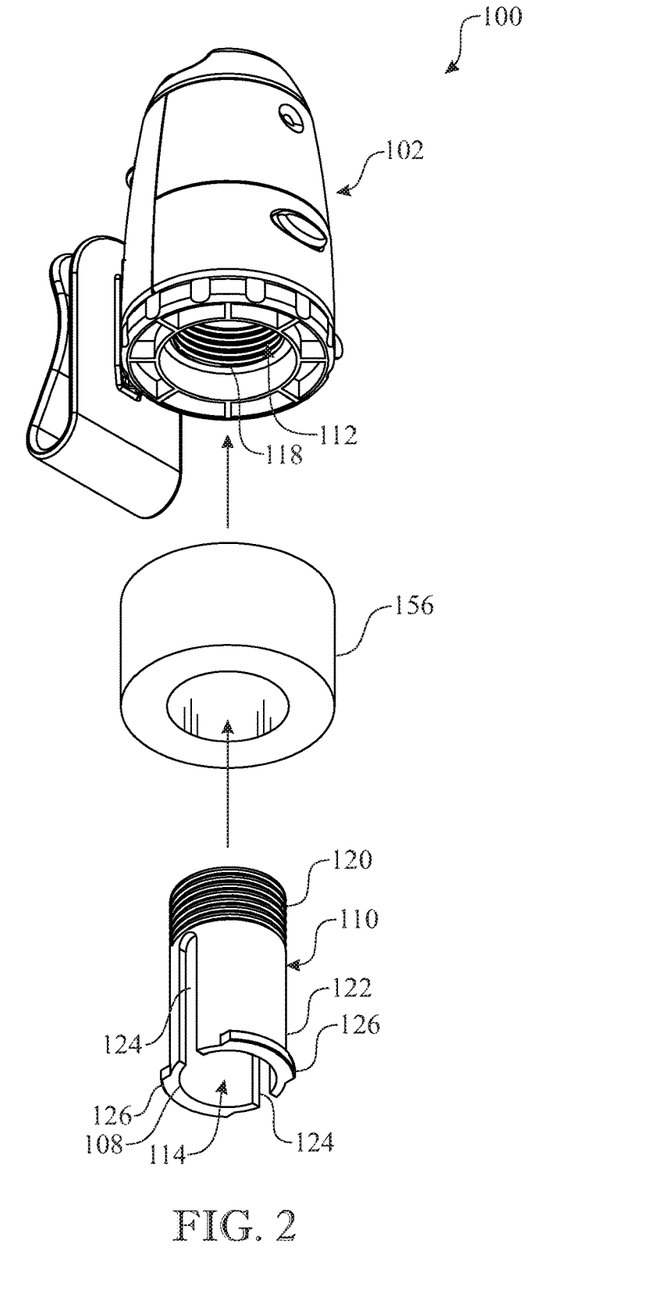
FIG. 2 presents a front isometric exploded view of the multi-accessory tool originally introduced in FIG. 1.
Figure 4:
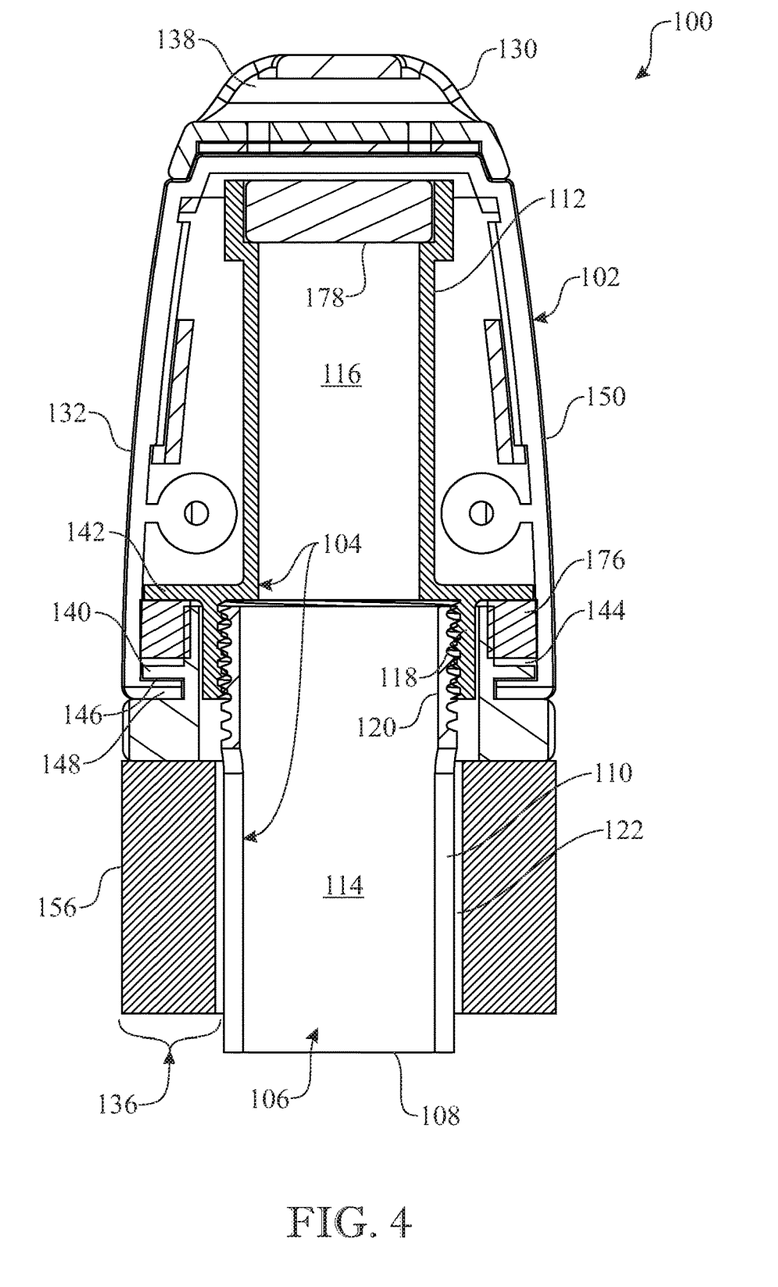
FIG. 4 presents a longitudinal section view of the multi-accessory tool taken along section line 4—4 in FIG. 1.

The multi-accessory tool 100 includes a platform 128 defining a lower end of the body 102 in engagement with a bottom end of the body 102 (as clearly shown in FIG. 4), an end cap 130 defining a top end of the body, and a body sidewall 132 extending therebetween. The platform 128 has an annular configuration defining a central opening 134 through which the externally threaded top end section 120 of the lower shaft portion 110 passes, or extends, enabling externally-threaded section 120 to be threaded onto or unthreaded from, the internally-threaded bottom end section 118 of the upper shaft portion 112. The body 102—including the sidewall 132, end cap 130, and platform 128—is supported about the upper shaft portion 112 of the elongated shaft 104 with the platform 128 of the body in a displaced relationship above the lower opening 108 of the lower shaft portion 110, thereby defining an annular space 136, or gap, exteriorly of the bottom end section 122 of the lower shaft portion 110 of the elongated shaft 104 extending from a lower surface of the platform 128 and an upper surface of the outwardly-projecting protrusions 126 at the lowermost end of elongated shaft lower portion 110, as best shown in FIGS. 2 and 4. The end cap 130 of the body 102 has a passageway 138 adapted to receive a health care attachment accessory therethrough, such as a lanyard (not shown) extending through the passageway in order to hang the tool 100 from the wearer's neck, etc.

Figure 3:
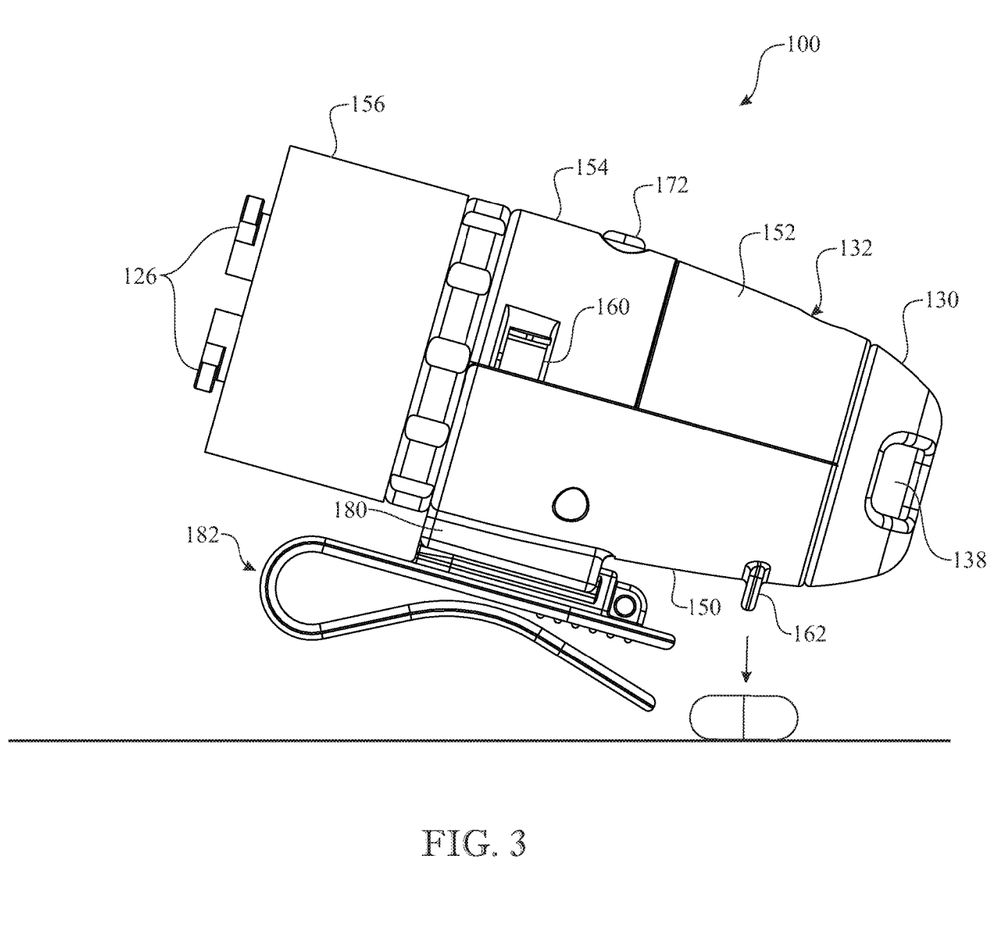
FIG. 3 presents a side isometric view of the multi-accessory tool originally introduced in FIG. 1, now illustrating a pill splitter on the tool aligned with a pill.
Figure 5:
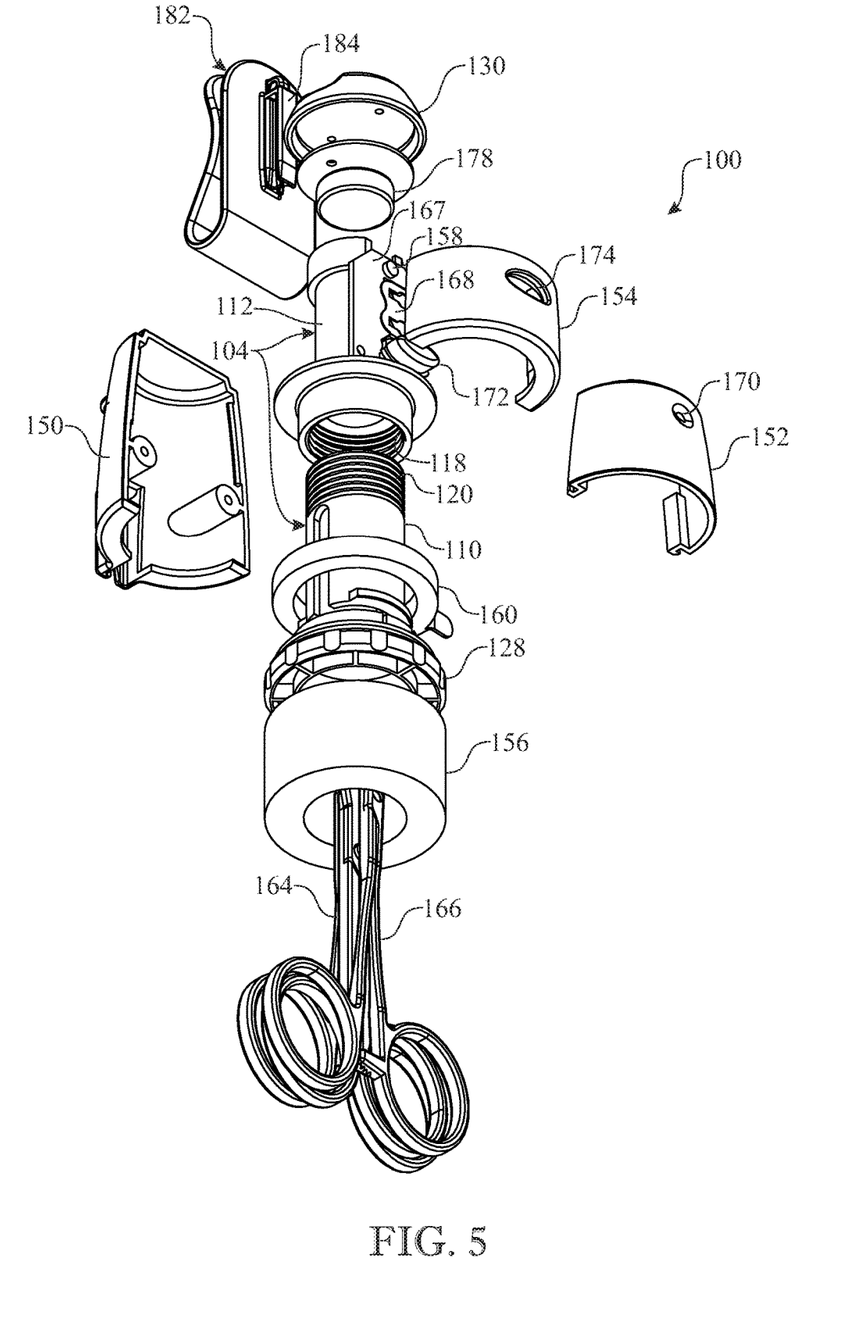
FIG. 5 presents a lower front isometric exploded view of the multi-accessory tool originally introduced in FIG. 1.
Figure 6:
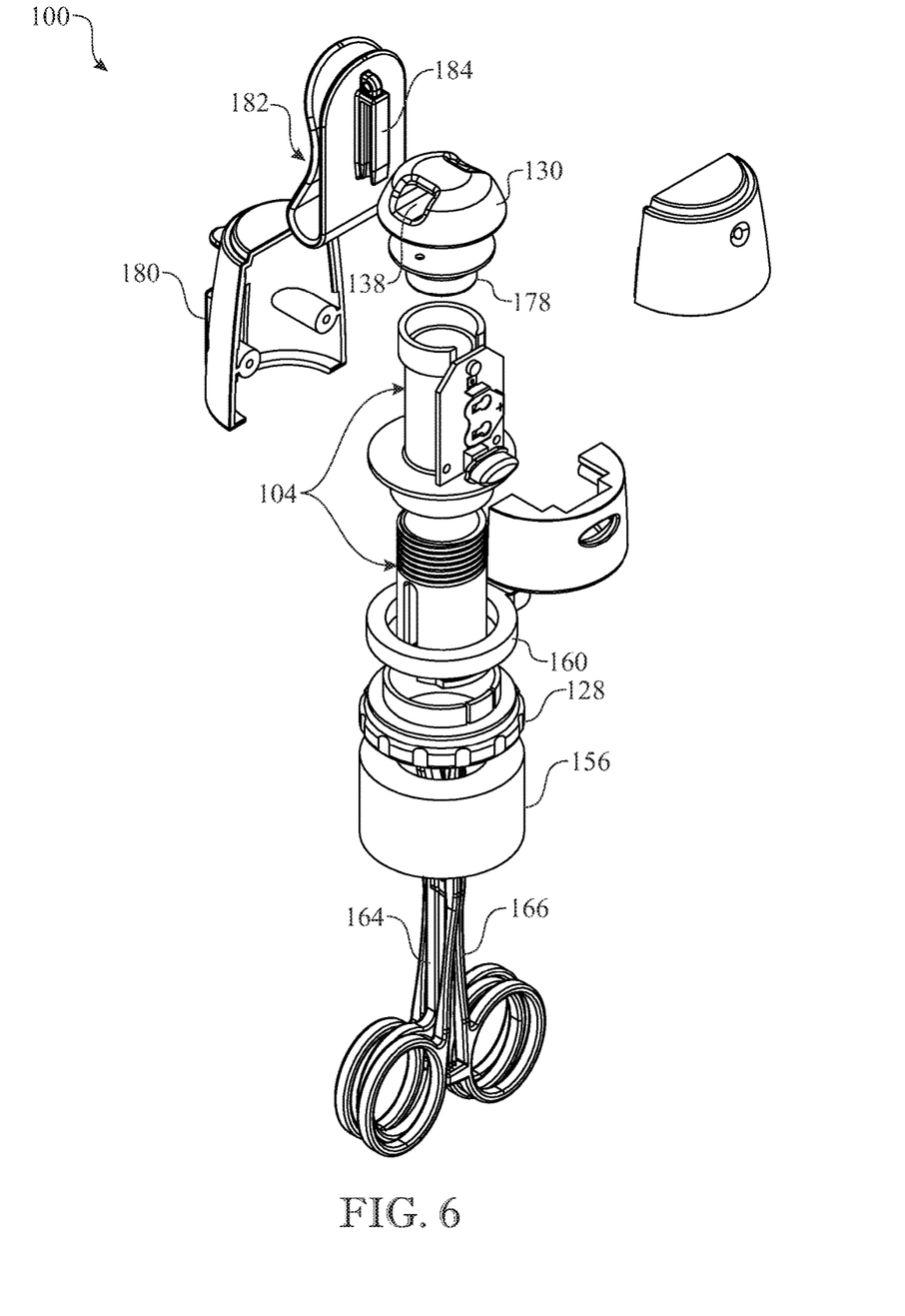
FIG. 6 presents an upper front isometric exploded view of the multi-accessory tool originally introduced in FIG. 1.

Referring now particularly to FIG. 4, platform 128 of body 102 includes an exterior ledge 140 of an annular configuration. Similarly, and the upper shaft portion 112 adjacent to the internally threaded bottom end section 118 thereof has an outwardly protruding flange 142 displaced a distance above the exterior ledge of the platform so as to define an annular chamber 144 about an interior surface of the sidewall 132 of the body 102. The platform 128 adjacent to and below the exterior ledge 140 thereof further defines a recess 146 of an annular configuration. The sidewall 132 of the body 102 at a lower end thereof has an inwardly protruding rim 148 that fits into the annular recess 146 of the platform 128. As best depicted in FIGS. 3, 5 and 6, sidewall 132 has a truncated conical configuration and includes a rear sidewall panel 150 that constitutes the back of the sidewall 132, and upper and lower sidewall panels, 152 and 154, respectively, that together constitute the front of the sidewall 132. The upper and lower sidewall panels, 152 and 154, respectively, are positioned one above the other, together extending between the platform 120 and the end cap 130.

The tool 100 is adapted to be attachable to a wearer and to mount or incorporate and hold a plurality of medical accessories. The accessories, or implements, mounted or incorporated by the tool 100 may be as follows: a roll 156 of medical tape, a LED light 158, a measuring tape 160, and a pill splitter 162. The accessories, or implements, held by the tool 100 are one or more hemostats 164 and scissors 166.

The annular space 136 is adapted to incorporate the roll 156 of medical tape supported by the pair of protrusions 126 and rotatable relative to the lower shaft portion 110 so as to enable external exposure of a strip of medical tape allowing it to be pulled and severed from the roll 156 in normal use. Changing the roll 156 of tape is accomplished by simply unscrewing the lower shaft portion 110 from the upper shaft portion 112, removing the core of the depleted roll from around the lower shaft portion 110, inserting a new roll 156 of medical tape on the lower shaft portion, and re-screwing the lower shaft portion 110 holding the new roll 156 back into the upper shaft portion 112.

The LED light 158 is mounted on a plate 167 behind the upper front sidewall panel 152 standing upright on the outwardly-protruding annular flange 142 at the bottom end section 118 of the upper shaft portion 112. The upper front sidewall panel 152 is removable from the body 102 to enable access to a battery 168 that powers the LED light 158. The LED light 158 is positioned such that it extends through an aperture 170 in the upper front sidewall panel 152 when the latter is replaced on the body 102. The LED light 158 is illuminated by a positive action button 172 that is positioned such that it extends through an aperture 174 in the lower front sidewall panel 154, wherein the button must be depressed to communicate power from the battery to the LED to enable illumination thereof. The LED light 158 remains in an off state when the button 172 is not being depressed.

Figure 7:
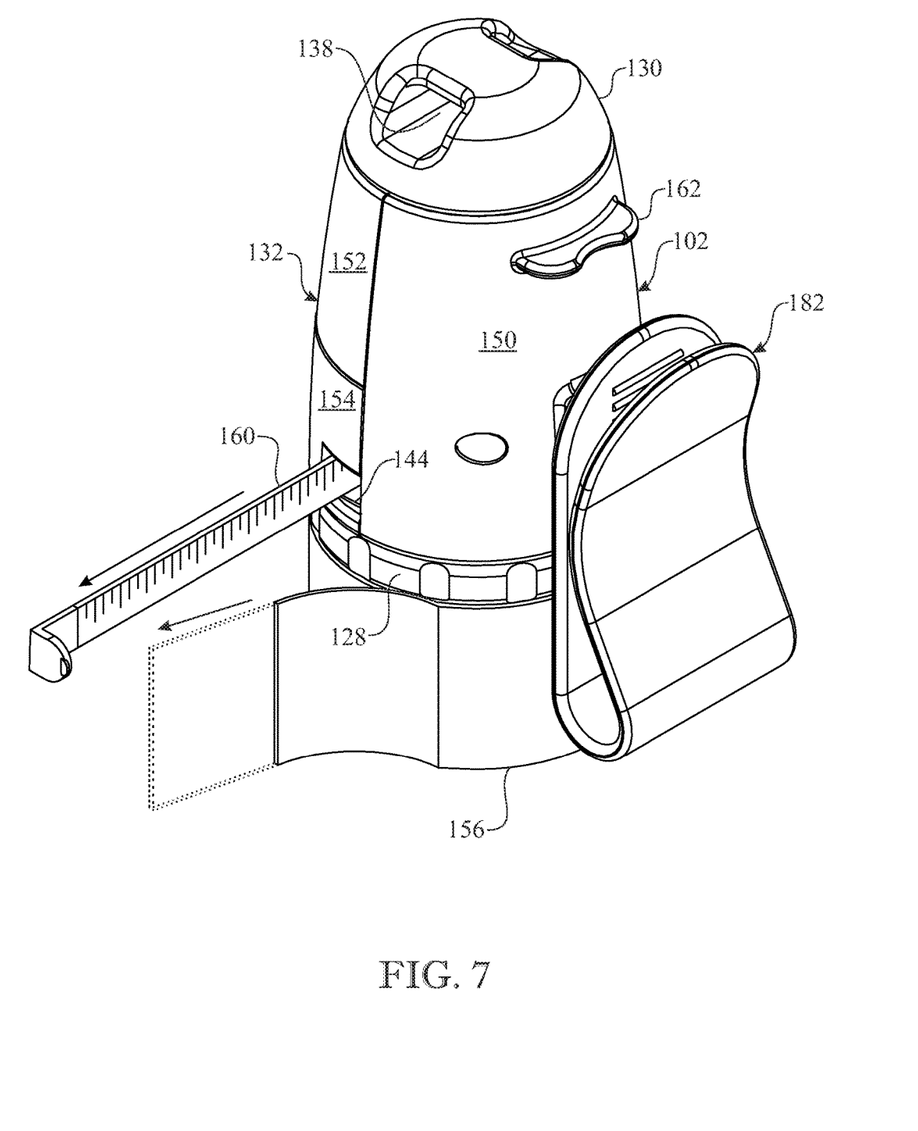
FIG. 7 presents a back isometric view of the multi-accessory tool originally presented in FIG. 1, now illustrated with a measuring tape accessory extended from the body of the tool.
Figure 8:
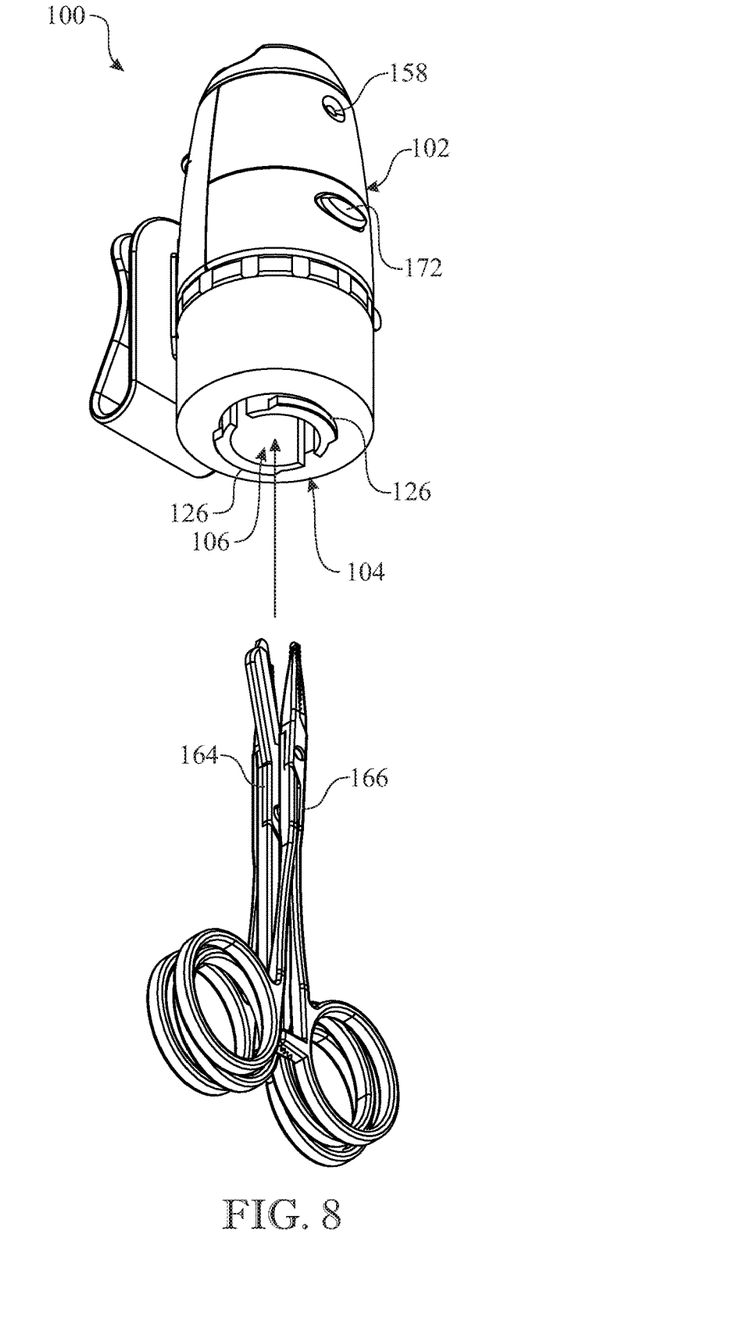
FIG. 8 presents a back isometric view of the multi-accessory tool originally introduced in FIG. 1, now illustrated with hemostat and scissor accessories withdrawn from the body of the tool.
Figure 9:
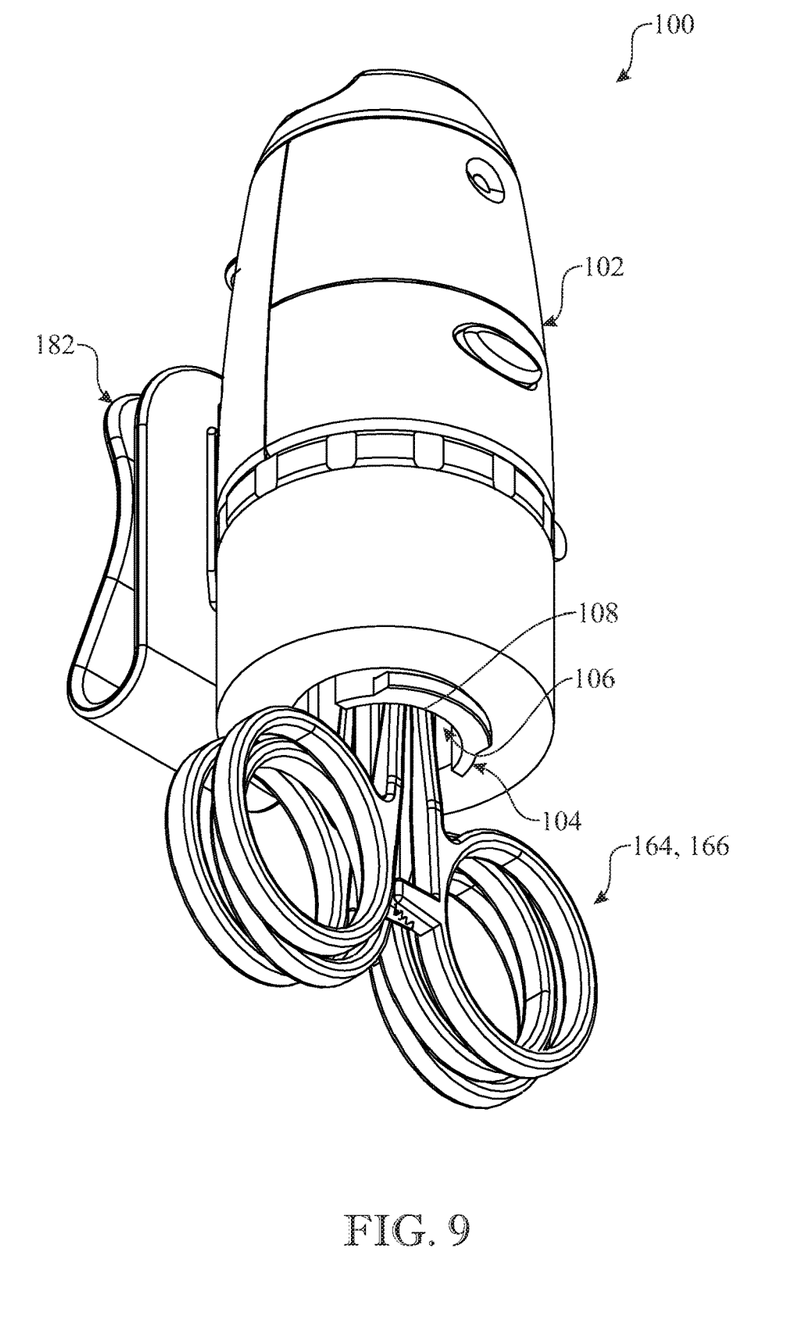
FIG. 9 presents a back isometric view of the multi-accessory tool originally presented in FIG. 1, now illustrated with the hemostat and scissor accessories inserted into the body of the tool.
Figure 10:
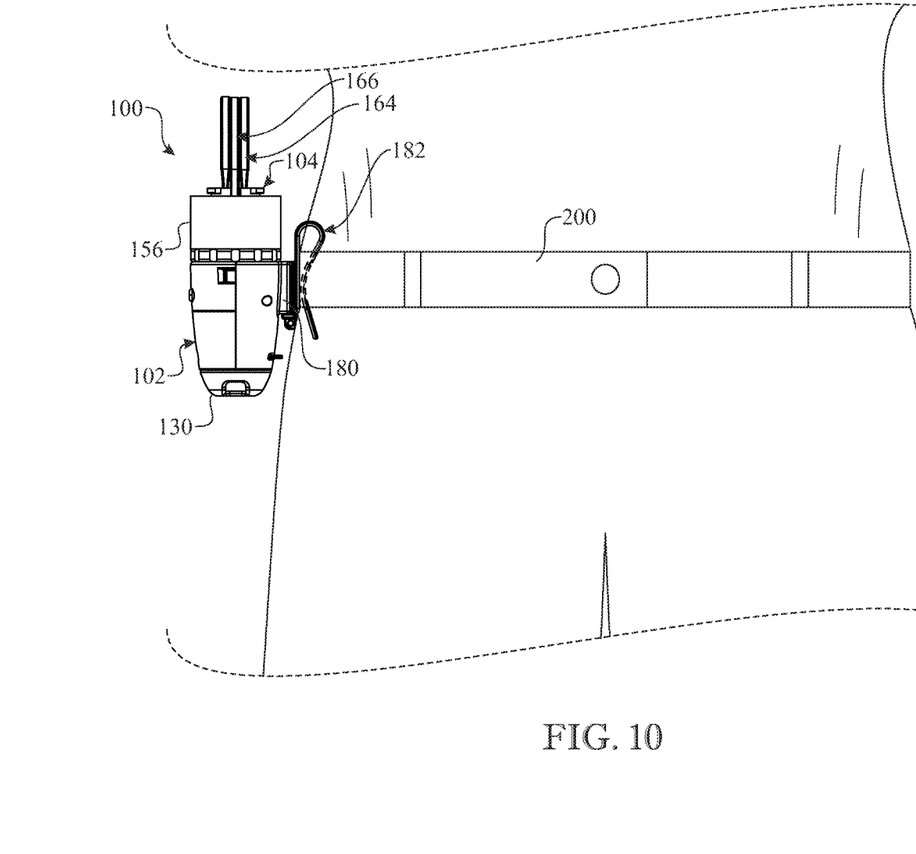
FIG. 10 presents a front side view of the multi-accessory tool originally introduced in FIG. 1, now illustrated mounted by a clip on a belt of a wearer.

The measuring tape 160 emanates from a rewinding mechanism body 176 incorporated in the annular chamber 144 of the body 102 interiorly of sidewall 132, as best shown in FIG. 4. The measuring tape 160 may be conveniently operated by a user grasping its forward end and pulling outwardly to deploy the desired length of measuring tape, as best shown in FIG. 7. Alternatively, an extended length of measuring tape may be retracted back into the interior of body 102, for example, by jerking on the measuring tape to initiate operation of the rewinding mechanism, as shown in FIG. 3.

As best shown in FIG. 3, the pill splitter 162 may be implemented in the form of a tab-like protrusion extending outwardly from an exterior surface of, for example, an upper portion of the rear sidewall panel 150 of the body 102 adjacent to the end cap 130. The user may employ the pill splitter 162 by pressing down on a scored pill inside its packaging in order to crack the pill in half. As seen in FIGS. 4-6, 8 and 9, the shank and related distal portions above the finger rings and ratchet portions of conventional hemostats 164, and the blade or any related portions above the handle portions of scissors 166, are preferably retained inserted within the interior open cavity 106 of the elongated shaft 104, via the magnetic attractive force of a magnet 178 seated within, or otherwise supported at a top end of, the distal end of the upper shaft portion 112 of elongated shaft 104, thereby ensuring that the metal implements are fully inserted into the body 102 of the tool 100, with the scissor handles and the hemostat finger rings remaining exposed to facilitate their selective extraction from the tool 100 as desired by a user. In addition to the aforementioned magnetic means for holding the metal tools in place, a resilient insert (e.g. foam, rubber, etc.) having a slit or any other effective opening extending therethrough may be inserted into the lower opening 108 of elongated shaft 104 (i.e. plugging the lower opening) to further aid with the retention of the metal instruments. In fact, such a resilient plug may enable selective retention of other elongated medical instruments, metallic or not, in addition to or in lieu of scissors and hemostats.

Significantly, the multi-accessory tool 100 of the present invention is intended to be carried upon the body of medical personnel in a manner that is unobtrusive and which maintains the corresponding accessories such that they can be promptly and conveniently accessed. Accordingly, the tool 100 incorporates two different means of attachment: a clip 182 having an attachment hook 184 secured to rear sidewall panel 150 to facilitate selective attachment to medical personnel clothing pockets, a waistline, a belt 200, or any other clothing feature to which the clip may be selectively secured; and a lanyard or similar cord-based attachment mechanism (not shown) secured to end cap passageway 138, which may be hung around a user's neck, tied about a user's forearm or other extremity.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A wearable multi-accessory tool for health care professionals, comprising:
    a body having a truncated conical geometry and configured to incorporate a plurality of health care related accessories, the body extending longitudinally about a central axis and comprising:
        a plurality of sidewall panels adjoined to one another to form a closed-top, open-bottom tool housing defining an interior space;
        an end cap seated upon the closed top of said body; and
        a platform having a generally annular geometry, the platform releasably-engaging a lower end of said adjoined sidewall panels and depending downwardly beyond the lower end of said adjoined sidewall panels;
    an elongated tubular shaft extending longitudinally about the central axis of said body, the elongated tubular shaft comprising:
        an upper shaft portion disposed within the interior space defined by said adjoined sidewall panels, the elongated tubular shaft; and
        a lower shaft portion releasably-attached to said upper shaft portion, said lower shaft portion having a bottom end section terminating at a lower end having at least one protrusion extending radially-outward therefrom, the at least one protrusion located a distance below said platform to define a gap between the platform and the at least one protrusion, said bottom end section of said lower shaft portion extending between said platform and said at least one protrusion sized, shaped, and otherwise configured to enable an annular-shaped roll of medical tape to be mounted about said lower shaft portion in such a manner that the tape roll is supported from below by said at least one protrusion, and a central core opening of the annular-shaped tape roll has an internal diameter nominally greater than a corresponding external diameter of the lower shaft portion, thereby enabling the tape roll to rotate about the lower shaft portion as a user of the tool removes a desired length of the tape; and a magnet secured proximate to an open upper end of the upper shaft portion of said elongated tubular shaft, said magnet functioning to exert a magnetic attractive force against a distal end of at least one elongated metal tool inserted through an opening at a lower end of the lower portion of said elongated tubular shaft.

2. A wearable multi-accessory tool as recited in claim 1, wherein said upper and lower shaft portions of said elongated shaft are threadably attached to one another, and said upper shaft portion is fixedly secured to said tool body, thereby enabling a user to easily thread the lower shaft portion in a first direction to attach the lower shaft portion to the upper shaft portion, and to thread the lower shaft portion in an opposite second direction to detach the lower shaft portion from the upper shaft portion.

3. A wearable multi-accessory tool as recited in claim 2, wherein the upper shaft portion of said elongated shaft further comprises:
a flange protruding radially-outward from a lower end portion thereof; and
an internally-threaded cylindrical wall depending downwardly from a bottom surface of said flange, said internally-threaded cylindrical wall threadably-engagable to a corresponding externally-threaded top end section of said lower shaft portion.

4. A wearable multi-accessory tool as recited in claim wherein said platform further comprises:
a generally annular-shaped base;
a cylindrical sidewall extending vertically upward from an upper surface of said base and terminating at an upper edge adjoining interior and exterior cylindrical sidewall surfaces; and
an annular-shaped exterior ledge extending radially outward from the exterior cylindrical sidewall surface a distance above the upper surface of the annular base to define a platform annular recess.

5. A wearable multi-accessory tool as recited in claim 4, wherein said lower end of said adjoined sidewall panels of said tool body further comprises:
an inwardly-protruding rim received within the annular recess of said platform;
an annular-shaped chamber sized, shaped, and otherwise configured for receiving a retractable tape measure body, said annular-shaped chamber defined by an upper surface of said platform exterior ledge, an area of the exterior cylindrical sidewall surface of said platform located above said inwardly-protruding platform rim, an area of the bottom surface of said upper shaft portion rim located exteriorly of the downwardly-depending internally-threaded cylindrical sidewall, and an interior surface of said sidewall located between said upper shaft portion rim and said platform exterior ledge; and
an opening extending completely through one of said plurality of sidewall panels to enable both the extension and retraction of a length of tape of said tape measure therethrough.

6. A wearable multi-accessory tool as recited in claim 1, wherein said upper end of said upper shaft portion of said elongated tubular shaft further comprises an increased-diameter open upper end defining a magnet-supporting and retention shoulder in which said magnet is seated.

7. A wearable multi-accessory tool as recited in claim 1 wherein said plurality of sidewall panels further comprise:
a rear sidewall panel;
a lower front sidewall panel; and
an upper front sidewall panel.

8. A wearable multi-accessory tool as recited in claim 7, further comprising:
a battery;
a light-emitting diode (LED); and
a positive action button;
said battery, said LED, and said positive action button all mounted to a plate fixedly supported within the interior of said body such that the battery, the LED, and the positive action button are in electrical communication with one another, wherein illumination of said LED only occurs while said positive action button is being depressed by a user of said multi-accessory tool.

9. A wearable multi-accessory tool as recited in claim 8 wherein said plurality of sidewall panels further comprise:
a rear sidewall panel having an attachment clip affixed thereto;
a lower front sidewall panel having an aperture extending completely therethrough, the lower front sidewall panel aperture sized nominally greater than that of said positive action button and shaped to conform to a periphery of the positive action button, the positive action button located such that it is surrounded by, and extends at least partially through, the lower front sidewall panel aperture when said tool is fully assembled; and
an upper front sidewall panel having an aperture extending completely therethrough, the upper front sidewall panel aperture sized nominally greater than that of said LED and shaped to conform to a periphery of the LED, the LED located such that it is surrounded by, and extends at least partially through, the upper front sidewall panel aperture when said tool is fully assembled.

10. A wearable multi-accessory tool as recited in claim 1 wherein the end cap seated upon the closed top of said body further comprises a passageway extending laterally therethrough, the passageway configured for attachment of a lanyard thereto.

11. A wearable multi-accessory tool as recited in claim 6 wherein the lower and upper shaft portions of the elongated shaft have respective interior diameters and respective lengths particularly sized to accommodate the insertion and subsequent retention of a plurality of elongated metal accessories therein, wherein said retention is at least partially the result of magnetic coupling of distal ends of said accessories with said magnet secured proximate to the open upper end of the upper shaft portion of said elongated tubular shaft.

12. A wearable healthcare multi-accessory tool, comprising:
a body of a truncated conical configuration adapted to support a plurality of health care attachment and illumination accessories; and
an elongated shaft of a tubular configuration having an interior open cavity and a lower opening to enable insertion of at least one of a hemostat and scissor into said interior open cavity via said lower opening;
wherein said elongated shaft comprises
an upper shaft portion extending through said body and having an internally threaded bottom end section, and
a lower shaft portion having an externally threaded top end section threaded into said internally threaded bottom end section of said upper shaft portion such that said lower shaft portion extends downward and in axial alignment with said upper shaft portion, said lower shaft portion also having a bottom end section extending downward from said top end section to said lower opening of said elongated shaft and at least one protrusion on said lower shaft portion adjacent to said lower opening such that said upper shaft portion supports said body about said upper shaft portion in a displaced relationship above said lower opening of said elongated shaft and said at least one protrusion on said lower shaft portion so as to provide an annular space surrounding said lower shaft portion below and recessed relative to the exterior of said body on said upper shaft portion to enable incorporation of a roll of health care tape in said annular space and supported on said at least one protrusion on said lower shaft portion adjacent to said lower opening such that the roll is rotatable about said lower shaft portion to further enable a strip of health care tape to be pulled and severed from said roll;

further wherein said body includes a plurality of adjoined sidewall panels, and a lower end of said adjoined sidewall panels of said tool body further comprises:

an inwardly-protruding rim received within the annular recess of said platform;

an annular-shaped chamber sized, shaped, and otherwise configured for receiving a retractable tape measure body, said annular-shaped chamber defined by an upper surface of said platform exterior ledge, an area of the exterior cylindrical sidewall surface of said platform located above said inwardly-protruding platform rim, an area of the bottom surface of said upper shaft portion rim located exteriorly of the downwardly-depending internally-threaded cylindrical sidewall, and an interior surface of said sidewall located between said upper shaft portion rim and said platform exterior ledge; and an opening extending completely through one of said plurality of sidewall panels to enable both the extension and retraction of a length of tape of said tape measure therethrough further wherein said body comprises a platform at a bottom end of said body having an annular configuration defining an interior opening such that said upper shaft portion extends through said interior opening of said platform, an end cap at a top end of said body being mounted above a closed top end of said upper shaft portion such that said end cap is adapted to support at least one of the plurality of health care attachment and illumination accessories, and a sidewall adapted to support the plurality of health care attachment and illumination accessories and being disposed between said platform and said end cap and surrounding said upper shaft portion.

13. The tool of claim 12 wherein said sidewall comprises a plurality of sidewall panels each adapted to support at least one of the plurality of health care attachment and illumination accessories.

14. The tool of claim 13 wherein said plurality of sidewall panels includes a rear sidewall panel adapted to support a pill splitter.

15. The tool of claim 13 wherein said plurality of sidewall panels includes an upper front sidewall panel being removable from said body so as to expose a battery-powered LED light supported on said body and aligned to seat in an aperture in said upper front sidewall panel when replaced on said body.

16. The tool of claim 13 wherein said plurality of sidewall panels includes a lower front sidewall panel being removable from said body so as to expose a positive action button supported on said body and aligned to seat in an aperture in said lower front sidewall panel when replaced on said body, said positive action button being operable to turn on and off said LED light.

17. The tool of claim 13 wherein said plurality of sidewall panels includes a rear sidewall panel having an attachment receptacle on the exterior of said rear sidewall panel; and also comprising a clip having an attachment hook selectively insertable and removable into and from said attachment receptacle.

18. A wearable healthcare multi-accessory tool, comprising:

a body of a truncated conical configuration adapted to support a plurality of health care attachment and illumination accessories; and an elongated shaft of a tubular configuration having an interior open cavity and a lower opening to enable insertion of at least one of a hemostat and scissor into said interior open cavity via said lower opening;

wherein said elongated shaft comprises an upper shaft portion extending through said body, said upper shaft portion having an internally threaded bottom end section and an upper end section holding a magnet to releasably retain the at least one of the hemostat and scissor in said interior open cavity of said elongated shaft, and a lower shaft portion having an externally threaded top end section threaded into said internally threaded bottom end section of said upper shaft portion such that said lower shaft portion extends downward and in axial alignment with said upper shaft portion, said lower shaft portion also having a bottom end section extending downward from said top end section to said lower opening of said elongated shaft and at least one protrusion on said lower shaft portion adjacent to said lower opening such that said upper shaft portion supports said body about said upper shaft portion in a displaced relationship above said lower opening of said elongated shaft and said at least one protrusion on said lower shaft portion so as to provide an annular space surrounding said lower shaft portion below and recessed relative to the exterior of said body on said upper shaft portion to enable incorporation of a roll of health care tape in said annular space and supported on said at least one protrusion on said lower shaft portion adjacent to said lower opening such that the roll is rotatable about said lower shaft portion to further enable a strip of health care tape to be pulled and severed from said roll;

further wherein said body comprises a platform at a bottom end of said body having an annular configuration defining an interior opening such that said upper shaft portion extends through said interior opening of said platform, an end cap at a top end of said body being mounted above a top end of said upper shaft portion such that said end cap is adapted to support at least one of the plurality of health care attachment and illumination accessories, and a sidewall adapted to support the plurality of health care attachment and illumination accessories and being disposed between said platform and said end cap and surrounding said upper shaft portion;

still further wherein said sidewall has an attachment receptacle on the exterior thereof and also comprising a clip having an attachment hook selectively insertable and removable into and from said attachment receptacle.

19. The tool of claim 18 wherein said platform also has an exterior ledge of an annular configuration, and said upper shaft portion adjacent to said internally threaded bottom end section thereof has an outwardly protruding flange displaced above said exterior ledge of said platform so as to define an annular chamber inside said sidewall in which to house a tape measure so as to be extendible and retractable from and into said annular chamber.

20. The tool of claim 19 wherein said platform of said body adjacent to and below said exterior ledge thereof has a recess of an annular configuration and said sidewall of said body at a lower end thereof has an inwardly protruding rim that fits into said annular recess of said platform.

* * * * *